United States Patent
Harada et al.

(10) Patent No.: US 9,187,404 B2
(45) Date of Patent: Nov. 17, 2015

(54) METHOD FOR PRODUCING POLYALKYLENE GLYCOL DERIVATIVE HAVING AMINO GROUP AT END, WITH NARROW MOLECULAR WEIGHT DISTRIBUTION

(71) Applicant: Shin-Etsu Chemical Co., Ltd., Tokyo (JP)

(72) Inventors: Yuji Harada, Joetsu (JP); Yuki Suka, Joetsu (JP); Osamu Watanabe, Joetsu (JP); Takeru Watanabe, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/596,704

(22) Filed: Jan. 14, 2015

(65) Prior Publication Data

US 2015/0197482 A1    Jul. 16, 2015

(30) Foreign Application Priority Data

Jan. 16, 2014 (JP) ................................. 2014-006075

(51) Int. Cl.
| | |
|---|---|
| *C07C 213/02* | (2006.01) |
| *C07C 213/10* | (2006.01) |
| *C07C 29/70* | (2006.01) |
| *C07C 253/30* | (2006.01) |
| *C08G 65/322* | (2006.01) |
| *C08G 65/333* | (2006.01) |
| *C07C 29/60* | (2006.01) |

(52) U.S. Cl.
CPC ............ *C07C 213/02* (2013.01); *C07C 29/60* (2013.01); *C07C 29/70* (2013.01); *C07C 29/705* (2013.01); *C07C 213/10* (2013.01); *C07C 253/30* (2013.01); *C08G 65/322* (2013.01); *C08G 65/333* (2013.01)

(58) Field of Classification Search
CPC .................................................. C07C 213/02
See application file for complete search history.

(56) References Cited

U.S. PATENT DOCUMENTS

| | | | |
|---|---|---|---|
| 3,268,587 A | 8/1966 | de Vries | |
| 5,510,103 A | 4/1996 | Yokoyama et al. | |
| 5,789,490 A * | 8/1998 | Chang | 525/403 |
| 6,455,639 B1 | 9/2002 | Yasukohchi et al. | |
| 6,576,794 B2 * | 6/2003 | Fukushima et al. | 564/292 |
| 7,728,175 B1 | 6/2010 | Qi et al. | |
| 2001/0000510 A1 | 4/2001 | Sakurai et al. | |
| 2006/0074200 A1 | 4/2006 | Daugs et al. | |
| 2011/0245509 A1 | 10/2011 | Nakamoto et al. | |

FOREIGN PATENT DOCUMENTS

| | | |
|---|---|---|
| EP | 0985697 | 3/2000 |
| EP | 2586811 | 5/2013 |
| JP | H08165343 A | 6/1996 |
| JP | 2690276 B2 | 12/1997 |
| JP | 2777530 B2 | 7/1998 |
| JP | 11-335267 | 12/1999 |
| JP | 3050228 B2 | 6/2000 |
| JP | 3562000 | 6/2004 |
| JP | 4987719 B2 | 7/2012 |
| WO | WO 97/30103 | 8/1997 |
| WO | WO 03/040211 | 5/2003 |
| WO | WO 2004/022630 | 3/2004 |

OTHER PUBLICATIONS

Extended European Search Report corresponding to European Application No. 15151526.9 dated Jun. 8, 2015.
Extended European Search Report corresponding to European Application No. 15151528.5 dated Jun. 1, 2015.

* cited by examiner

*Primary Examiner* — Brian J Davis
(74) *Attorney, Agent, or Firm* — Myers Bigel Sibley & Sajovec, P.A.

(57) ABSTRACT

A method for producing a narrow molecular weight distribution polyalkylene glycol derivative having an amino group at an end under mild conditions. A method for producing a compound of the general formula (1): $CH_3O(CH_2CH_2O)_nCH_2CH_2CH_2NH_2$ (wherein n is an integer of 1 to 450) comprises the following steps of:

1) a step of producing a compound of the general formula (3): $CH_3O(CH_2CH_2O)_{k-1}CH_2CH_2O^-M^+$ from a compound of the general formula (2): $CH_3O(CH_2CH_2O)_kH$ (wherein k is an integer of 2 to 5);
2) a step of producing a compound of the general formula (4): $CH_3O(CH_2CH_2O)_{n-1}CH_2CH_2O^-M^+$ from a compound of the general formula (3);
3) a step of reacting a compound of the general formula (4) with acrylonitrile to obtain a compound of the general formula (5): $CH_3O(CH_2CH_2O)_nCH_2CH_2CN$; and
4) a step of reducing a compound of the general formula (5) to obtain a compound of the general formula (1).

17 Claims, No Drawings

METHOD FOR PRODUCING POLYALKYLENE GLYCOL DERIVATIVE HAVING AMINO GROUP AT END, WITH NARROW MOLECULAR WEIGHT DISTRIBUTION

RELATED APPLICATION

This application claims priority from Japanese Patent Application No. 2014-006075, filed Jan. 16, 2014, the disclosure of which is incorporated by reference herein in its entirety.

FIELD AND BACKGROUND OF THE INVENTION

The present invention relates to a method for producing a narrow molecular weight distribution polyalkylene glycol derivative having an amino group at an end.

Recently, in the drug delivery system, a method for encapsulating drugs in a polymer micelle using a block copolymer formed from a hydrophilic segment and a hydrophobic segment has been proposed (refer to, for example, Japanese Patent No. 2690276, Japanese Patent No. 2777530, and Japanese Patent Application Laid-Open Application No. 11-335267). By using the method, the polymer micelle functions as a carrier of drugs, producing various effects including sustained release in vivo and concentrated dosage to an affected region.

As the hydrophilic segment, many examples with use of a polyalkylene glycol skeleton are proposed (refer to, for example, Japanese Patent No. 2690276, Japanese Patent No. 2777530, and Japanese Patent Application Laid-Open No. 11-335267). A compound having a polyalkylene glycol skeleton has low toxicity in vivo, and enables excretion in kidney to be delayed. Consequently, in comparison with a compound having no polyalkylene glycol skeleton, the retention time in blood can be prolonged. As a result, with use of a drug micellized with a polyalkylene glycol derivative, the dosage amount or dosage frequency can be reduced.

Among polyalkylene glycol derivatives, a compound having an amino group at an end can lead to a block copolymer composed of a polyalkylene glycol skeleton and an amino acid skeleton through a ring-opening polymerization reaction with α-amino acid-N-carboxyanhydride. Many examples with use of the produced block copolymer for encapsulating drugs in a polymer micelle are proposed (refer to, for example, Japanese Patent No. 2690276, Japanese Patent No. 2777530, and Japanese Patent Application Laid-Open Application No. 11-335267).

Synthesis methods of such polyalkylene glycol derivatives having an amino group at an end are also known (refer to, for example, Japanese Patent No. 3050228 and Japanese Patent No. 3562000). In these methods, after polymerization of alkylene oxide with use of a metal salt of monohydric alcohol as a polymerization initiator, a polymer end is converted to a hydroxyl group, and then to a 2-cyanoethoxy group, finally leading to an amino group-containing substituent group (3-amino-1-propoxy group) through hydrogen reduction of the cyano group.

A polymerization example of ethylene oxide in diglyme with use of a potassium salt of substituted diethylene glycol is known, in which the necessary reaction temperature is specified to be 80 to 140° C. with use of diethylene glycol monomethyl ether as co-solvent (with reference to, for example, Japanese Patent No. 4987719).

SUMMARY OF THE INVENTION

It is difficult to completely dissolve the metal salts of monohydric alcohol in tetrahydrofuran (THF) in many cases. In order to dissolve the metal salts in polymerization solvent, a co-solvent such as methanol and ethanol is required. Due to the presence of these alcohols in a reaction system, however, reduction in the polymerization rate is unavoidable. Consequently, crucial reaction conditions such as high temperature and high pressure are required for increasing the polymerization rate. This is as disclosed in Japanese Patent No. 4987719.

Monohydric alcohols contain a trace amount of water in many cases. The polymerization of alkylene oxide with a polymerization initiator prepared in a water-containing state produces a polymer compound having a hydroxyl group at both ends as by-product (hereinafter abbreviated as diol polymer). In the case of monohydric alcohols having a boiling point sufficiently higher than that of water, the water content can be reduced by dehydration under reduced pressure. Since methanol for use in a case where an end is a methyl group has a boiling point lower than that of water, the water content cannot be removed by dehydration under reduced pressure. The polymerization with a metal salt prepared by using methanol, therefore, unavoidably produces a diol polymer. Since various physical properties of diol polymer such as structure and molecular weight are similar to those of the target substance, is extremely difficult to separate and purify. When the subsequent reactions proceed in the presence of diol polymer as impurity, a polymer including an amino group at both ends is produced unless proper reaction conditions are selected. The direct use of the polymer which includes such an impurity may cause a possibility that an intended performance cannot be achieved in designing a polymer micellizing agent. In the polymerization reaction, therefore, the water content is required to be reduced as low as possible.

Several methods are conceivable to convert an end to a 2-cyanoethoxy group, and further to a 3-amino-1-propoxy group, after polymerization. In the method in Japanese Patent No. 3050228 and Japanese Patent No. 3562000, a polymer compound having a hydroxyl group at an end is once extracted to react with acrylonitrile in presence of a base, leading to have a 2-cyanoethoxy group. After conversion of a cyano group to an aminomethyl group by hydrogenation using a Raney nickel catalyst, the aqueous solution of produced amino group-containing polymer is purified with a cation exchange resin, and the aqueous solution is freeze dried to extract a target substance. However, there exist problems that freeze drying requires special facilities and, in addition, complete removal of water requires a long time. A method for solving the problems is therefore needed.

It is an object of the present invention, in view of the background, to provide a method for producing a narrow molecular weight distribution polyethylene glycol derivative having an amino group at an end. Use of the method of the present invention enables the polymerization of ethylene oxide under conditions milder than conventional ones and the suppression of formation of polymer impurities due to a trace amount of water. Furthermore, due to simplification of the reaction process and improvement in the purifying process, both of increase in yield rate and cut-down of process time can be achieved in parallel.

Through intensive study for achieving the object, the present inventors found that use of a polymerization initiator represented by the general formula (3) accomplishes the polymerization of ethylene oxide in THF under mild conditions and the suppression of formation of diol polymers. Furthermore, the present inventors found that due to simplification of the reaction process and improvement in the purifying process, both of increase in yield rate and cut-down of process time can be achieved in parallel. The present invention has been thus completed.

More specifically, the present invention relates to a method for producing a narrow molecular weight distribution polyethylene glycol derivative having an amino group at an end represented by a general formula (1) includes the following steps of:

$$CH_3O(CH_2CH_2O)_nCH_2CH_2CH_2NH_2 \quad (1)$$

wherein n represents an integer of 1 to 450.

1) a step of reacting a compound represented by the general formula (2) with an alkali metal compound selected from M, $M^+H^-$, and $RO^-M^+$ (wherein M represents sodium (Na) or potassium (K), and R represents a monovalent alkyl group having 1 to 6 carbon atoms) to obtain a compound represented by a general formula (3):

$$CH_3O(CH_2CH_2O)_kH \quad (2)$$

wherein k represents an integer of 2 to 5;

$$CH_3O(CH_2CH_2O)_{k-1}CH_2CH_2O^-M^+ \quad (3)$$

wherein k is the same as defined in the general formula (2); and

M is the same as defined for the alkali metal compound;

2) a step of dissolving a compound represented by the general formula (3) in tetrahydrofuran and then reacting with ethylene oxide to obtain a compound represented by the following general formula (4):

$$CH_3O(CH_2CH_2O)_{n-1}CH_2CH_2O^-M^+ \quad (4)$$

wherein n is the same as defined in the general formula (1);

3) a step of reacting an unpurified compound represented by the general formula (4) with acrylonitrile and then with an acid compound to obtain a compound represented by the general formula (5); and $$CH_3O(CH_2CH_2O)_nCH_2CH_2CN \quad (5)$$

4) a step of reducing a compound represented by the general formula (5) to obtain a compound represented by the general formula (1).

The present invention provides a method for producing an amino group-containing narrow molecular weight distribution polyethylene glycol derivative as a useful raw material for block copolymers for use in medical supplies and cosmetic products. Use of the method enables the polymerization of ethylene oxide under mild conditions and the suppression of formation of diol polymer impurities. Furthermore, due to simplification of the end modifying process and improvement in the purifying process, both of increase in yield rate and cut-down of process time can be achieved in parallel. Further, the polyalkylene glycol derivative produced by the production method of the present invention is narrow molecular weight distribution, capable of being extremely advantageously used in producing to a block copolymer formed from a hydrophilic segment and a hydrophobic segment, for use in a field of drug delivery system.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

In an embodiment of the present invention, the method for producing a narrow molecular weight distribution polyethylene glycol derivative having an amino group at an end includes sequentially performing the following [Step 1] to [Step 4]. Optionally, the method may further include [Step 5] to [Step 8]. The narrow molecular weight distribution polyethylene glycol derivative having an amino group at an end produced by the production method in the present embodiment is represented by the general formula (1).

$$CH_3O(CH_2CH_2O)_nCH_2CH_2CH_2NH_2 \quad (1)$$

wherein n represents an integer of 1 to 450.

In the narrow molecular weight distribution polyethylene glycol derivative having an amino group at an end represented by the general formula (1), i.e. the target substance of the production method of the present invention, n represents an integer of 1 to 450, preferably n=10 to 400, more preferably n=20 to 350. The molecular weight and the dispersity (Mw/Mn) of a polymer may be measured values by gel permeation chromatography (hereinafter abbreviated as GPC), respectively. The compound represented by the general formula (1) has a dispersity of, for example, 1.0 to 1.4, preferably 1.0 to 1.3, more preferably 1.0 to 1.2.

In the [Step 1], a compound represented by the general formula (2) is reacted with an alkali metal compound selected from M, $M^+H^-$, and $RO^-M^+$ (wherein M represents sodium (Na) or potassium (K), and R represents a monovalent alkyl group having 1 to 6 carbon atoms) to synthesize a compound represented by the general formula (3):

$$CH_3O(CH_2CH_2O)_kH \quad (2)$$

$$CH_3O(CH_2CH_2O)_{k-1}CH_2CH_2O^-M^+ \quad (3)$$

wherein M represents sodium or potassium, R represents a monovalent alkyl group having 1 to 6 carbon atoms, and k represents an integer of 2 to 5.

In the [Step 1], the alkali metal compound to be reacted with a compound represented by the general formula (2) means a substance selected from the group consisting of an alkali metal represented by M, a hydride of alkali metal represented by $M^+H^-$, and an alkali metal salt of monohydric alcohol represented by $RO^-M^+$ (wherein M represents sodium or potassium and R represents a monovalent alkyl group having 1 to 6 carbon atoms). Specific examples of the R include a methyl group, an ethyl-group, an n-propyl group, an isopropyl group, an n-butyl group, a sec-butyl group, a tert-butyl group, an n-pentyl group, an isopentyl group, and a hexyl group, although this is not limited thereto. The amount of the alkali metal represented by M, $M^+H^-$, or $RO^-M^+$ used is, for example, 0.5 to 3.0 equivalents, preferably 0.8 to 2.0 equivalents, more preferably 0.9 to 1.5 equivalents, relative to the number of moles of a compound represented by the general formula (2).

In synthesizing a compound represented by the general formula (3) in the [Step 1], a proper solvent can be used as needed. Specific examples of the solvent include ethers such as THF and 1,4-dioxane, and aromatic hydrocarbons such as benzene, toluene, and xylene. In the case of using a solvent, a solvent distilled with a dehydrating agent such as metal sodium may be used. The solvent has a water content ratio of, for example, 50 ppm or less, preferably 10 ppm or less, more preferably 5 ppm or less. The amount of the solvent used is, for example, 1 to 50 times, preferably 2 to 10 times, more preferably 2 to 5 times the mass of a compound represented by the general formula (2) although this is not limited thereto. The reaction may be performed at a temperature of, for example, −78 to 100° C., preferably at a temperature of 0° C. to the reflux temperature of the solvent for use. The reaction system may be cooled or heated as needed.

In the general formula (2) and the general formula (3), k is 2 to 5, preferably 2 to 3. As described above, the polymerization of alkylene oxide with a polymerization initiator prepared with a water-containing monohydric alcohol produces a diol polymer as by-product. Separation of a diol polymer from the target substance is extremely difficult. There is a high possibility that the intended performance of a polymer micellizing agent is not achieved with the direct use of the polymer which contains a diol polymer or impurities derived therefrom. In the polymerization reaction, therefore, the water content in the reaction system in which a compound (polymerization initiator) represented by the general formula (3) is dissolved is required to be reduced as low as possible. A compound represented by the general formula (2) with, for example, k=2, and a high boiling point of 194° C., has a sufficient difference in boiling point from water, so that separation of water can be achieved by drying under reduced pressure. In that case, it is preferred that prior to addition of an alkali metal compound, a compound represented by the general formula (2) is sufficiently dried under reduced pressure and then distilled. In that case, the water content ratio of the reaction system is reduced, for example, to 50 ppm or less, preferably 10 ppm or less, more preferably 5 ppm or less, for the reaction to proceed. In the viewpoint that a large amount of a high-purity compound represented by the general formula (2) is produced, having k=2 to 3 is particularly preferred.

In polymerization of ethylene oxide in THF, $CH_3O^-M^+$ (wherein M represents sodium or potassium) as conventional polymerization initiator commonly used is hardly dissolved in THF alone. A co-solvent such as methanol and ethanol is, therefore, required for homogeneous polymerization. Due to the presence of these alcohols in a reaction system, however, reduction in the polymerization rate is unavoidable. Consequently, crucial reaction conditions such as high temperature and high pressure are required for increasing the polymerization rate. In contrast, a compound represented by the general formula (3) for use as a polymerization initiator in the present invention is easily dissolved in THF without requiring a co-solvent, enabling polymerization under mild conditions. In order to achieve sufficient reaction rate under mild conditions in the subsequent step, the molar ratio between a compound represented by the general formula (2) and a compound represented by the general formula (3) present is preferably 0:100 to 20:80 after completion of the [Step 1]. For that purpose, preferably the [Step 1] is performed under conditions that the number of moles of the alkali metal compound used is 0.8 to 1.5, preferably 0.8 to 1.2, more preferably 0.9 to 1.0, of that of a compound represented by the general formula (2). In other words, in the step 1 of the present invention, a metal salt represented by the general formula (3) is not required to be 100% generated, with a raw material alcohol represented by the general formula (2) being remained (in the case of the molar ratio of a compound represented by the general formula (2)>0). Even when the complete conversion of raw material alcohol (2) to a metal salt (3) cannot be achieved, the raw material alcohol (2) functions also as a solvent of the metal salt (3), so that the polymerization can proceed smoothly. Alternatively, achieving the complete consumption of raw material alcohol (2) (in the case of a molar ratio of a compound represented by the general formula (2) to a compound represented by the general formula (3) of 0:100) has an advantage that the step 2 can be performed without use of an alcohol co-solvent as described below.

In the [Step 2], a compound represented by the general formula (3) is completely dissolved in the polymerization solvent of THF and then reacted with ethylene oxide at a temperature of 30 to 60° C., so that a compound represented by the general formula (4) is synthesized.

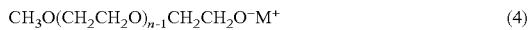

$$CH_3O(CH_2CH_2O)_{n-1}CH_2CH_2O^-M^+ \qquad (4)$$

In the [Step 2], the reaction mixture produced in the [Step 1] including a compound represented by the general formula (2) and a compound represented by the general formula (3) with a molar ratio of preferably 0:100 to 20:80 is directly dissolved in THF. The amount of THF used in the [Step 2] is, for example, 1 to 50 times, preferably 2 to 30 times, more preferably 3 to 20 times the mass of ethylene oxide used, although this is not particularly limited. Use of THF distilled with a dehydrating agent such as metal sodium is preferred. The water content ratio is, for example, 50 ppm or less, preferably 10 ppm or less, more preferably 5 ppm or less.

The compound represented by the general formula (3) for use as a polymerization initiator in the present invention is easily dissolved in THF without requiring a co-solvent of alcohols, being advantageously used for achieving polymerization under mild conditions. Accordingly the [Step 2] in the present invention is performed preferably without using an alcohol co-solvent.

As the addition method of ethylene oxide, ethylene oxide may be added in one batch to a reaction system with a compound represented by the general formula (3) dissolved in THF, or a solution of ethylene oxide dissolved in THF may be dripped into a reaction system. The polymerization reaction is performed at a temperature of, for example, 30 to 60° C., preferably 40 to 60° C., more preferably 45 to 60° C. The degree of progress of polymerization reaction can be monitored with GPC. When no change is observed in conversion ratio of ethylene oxide, the completion can be assumed.

In the [Step 3], the compound represented by the general formula (4) produced in the preceding step 2 is directly reacted with acrylonitrile at a reaction temperature of 20 to 60° C. without further purification step of the compound represented by the general formula (4), and then with an acid compound, so that a compound represented by the general formula (5) is synthesized.

$$CH_3O(CH_2CH_2O)_nCH_2CH_2CN \qquad (5)$$

Use of the compound represented by the general formula (4) without purification not only achieves cost reduction due to simplification of the separation purifying process, but also has an advantage of preventing reduction in yield rate due to purifying operation (polymer adhering to manufacturing equipment, dissolving in a poor solvent, and the like).

In this step, the reaction liquid in the [Step 2] may be directly used, or may be concentrated for use. In the case of concentration of the reaction liquid, the concentration of a compound represented by the general formula (4) is concentrated to, for example, 10 to 50 mass %, preferably 15 to 45 mass %, more preferably 20 to 40 mass %. In the reaction in the [Step 3], acrylonitrile is added to the reaction liquid or concentrated liquid after completion of the [Step 2] to be reacted. As the addition method of acrylonitrile, acrylonitrile may be added in one batch to a reaction system, or a solution of acrylonitrile dissolved in THF may be dripped. The amount of acrylonitrile used in the reaction is, for example, 1 to 50 equivalents, preferably 10 to 40 equivalents, more preferably 15 to 30 equivalents, relative to the number of moles of a compound represented by the general formula (4).

Although the reaction in the [Step 3] proceeds without a catalyst, a basic compound may be added for further acceleration of the reaction. In that case, examples of the basic compound include potassium hydroxide, sodium hydroxide, and potassium tert-butoxide, although this is not limited thereto. The amount of the basic compound added is, for example, 0.01 to 1 equivalent, preferably 0.01 to 0.5 equivalents, more preferably 0.01 to 0.3 equivalents, relative to the number of moles of a compound represented by the general formula (4).

In the [Step 3], the reaction is performed at a temperature of, for example, 20 to 60° C., preferably 20 to 50° C., more preferably 20 to 40° C. The reaction is monitored by NMR, and the completion can be assumed when no change is observed in conversion ratio.

After completion of the reaction in the [Step 3], the reaction mixture is neutralized with addition of an acid compound to obtain a compound represented by the general formula (5). Examples of the acid compound for use in the reaction include carboxylic acids such as formic acid, acetic acid, propionic acid, succinic acid, citric acid, tartaric acid, fumaric acid, malic acid, and trifluoroacetic acid, inorganic acids such as hydrochloric acid, sulfuric acid, nitric acid, phosphoric acid, and perchloric acid, and sulfonic acids such as benzenesulfonic acid and p-toluenesulfonic acid, and solid acids such as AMBERLYST SERIES made by Organo Corporation, although this is not limited thereto. The amount of the acid compound used is, for example, 1 to 5 equivalents, preferably 1 to 3 equivalents, more preferably 1 to 2 equivalents, relative to the number of moles of a compound represented by the general formula (4). These acid compounds may be used singly or in combinations of two or more. In that case, the mixing ratio is not particularly limited.

In order to separate an alkali metal salt produced by the neutralization reaction in the [Step 3], an alkali adsorbent may be used. Examples of the preferable alkali adsorbent for use include a synthesized magnesium silicate (e.g. KYOWADO 600 made by Kyowa Chemical Industry Co., Ltd.) and a synthesized aluminum silicate (e.g. KYOWADO 700 made by Kyowa Chemical Industry Co., Ltd.), although this is not limited thereto. The amount of the alkali adsorbent used is for example, 0.1 to 10 times, preferably 0.2 to 8 times, more preferably 0.3 to 6 times the mass of a compound represented by the general formula (5). After completion of the reaction, the alkali adsorbent can be removed by filtration.

In the case of a compound represented by the general formula (5) which is a reaction product of the [Step 3], the solid may be extracted for use prior to the subsequent step. In that case, the reaction liquid is, either directly or after concentration, dripped into a poor solvent to be crystallized. In the case of concentration, the concentration of a compound represented by the general formula (5) is adjusted to be, for example, 10 to 50 mass %, preferably 15 to 45 mass %, more preferably 20 to 40 mass %.

In concentration, solvent substitution with a good solvent for a compound represented by the general formula (1) may be performed for crystallization. In that case, specific examples of the good solvent include ethers such as 1,4-dioxane, aromatic hydrocarbons such as benzene, toluene, and xylene, esters such as ethyl acetate, n-butyl acetate, and γ-butyrolactone, ketones such as acetone, methyl ethyl ketone, and methyl isobutyl ketone, dimethyl sulfoxide (DMSO), N,N-dimethylformamide (DMF), and acetonitrile, although this is not limited thereto. These solvents may be used singly or in combinations of two or more. In that case, the mixing ratio is not particularly limited. The concentration after solvent substitution is, for example, 10 to 50 mass %, preferably 15 to 45 mass %, more preferably 20 to 40 mass %.

The poor solvent for use has a low solubility for a compound represented by the general formula (5). Specific examples of the suitable poor solvent for use include hydrocarbon such as hexane, heptane, octane, nonane, decane, cyclopentane, cyclohexane, cycloheptane, and cyclooctane, and ethers such as diethyl ether, diisopropyl ether, and di-n-butyl ether. The amount of the poor solvent used is, for example, 5 to 100 times, preferably 5 to 50 times, more preferably 5 to 20 times the mass of a compound represented by the general formula (5), although this is not particularly limited thereto. The poor solvents may be used singly or in combinations of two or more. Alternatively the poor solvent may be mixed with a different solvent for use. Examples of the different solvent for mixing include esters such as ethyl acetate, n-butyl acetate, and γ-butyrolactone, ketones such as acetone, methyl ethyl ketone, and methyl isobutyl ketone, hydrocarbons such as benzene, toluene, xylene, and cumene, ethers such as tetrahydrofuran, diethyl ether, and 1,4-dioxane, alcohols such as methanol, ethanol, isopropyl alcohol, and ethylene glycol monomethyl ether, dimethyl sulfoxide (DMSO), N,N-dimethylformamide (DMF), and acetonitrile, although this is not limited thereto. In the case of using a mixture of two or more solvents as a poor solvent, the mixing ratio is not particularly limited.

In the [Step 3], after precipitation of solid of the compound represented by the general formula (5) by crystallization, the solid may be washed for purification as needed. The solvent for use in washing is desirably the same poor solvent as described above, although this is not particularly limited, without particular limitation on the amount of the washing solvent used. The obtained solid is dried under reduced pressure, so that a compound represented by the general formula (5) can be extracted as solid.

In the [Step 4], a compound represented by the general formula (5) is reduced by hydrogenation reaction in a monohydric alcohol having 1 to 5 carbon atoms, so that a compound (crude product) represented by the general formula (1) is synthesized.

Examples of the monohydric alcohol for use in the [Step 4] may include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol. The monohydric alcohol solvents may be used singly or in combinations of two or more. In that case, the mixing ratio is not particularly limited. The amount of the monohydric alcohol used is, for example, 0.2 to 50 times, preferably 0.3 to 30 times, more preferably 0.4 to 20 times the mass of the compound represented by the general formula (5) although this is not limited thereto.

The reduction reaction is performed under hydrogen atmosphere, using a hydrogenation catalyst. Examples of the catalyst for suitable use include a Raney cobalt catalyst ("R-400" made by Nikko Rica Corporation), a Raney nickel catalyst ("R-211" and "R-2311" made by Nikko Rica Corporation), a supported gold-palladium catalyst ("NTA-25" made by N. E. CHEMICAT Corporation), although this is not particularly limited. The amount of the catalyst used is, for example, 0.1 to 5 times, preferably 0.2 to 3 times, more preferably 0.3 to 2 times the mass of a compound represented by the general formula (5), although this is not limited thereto. The hydrogenation catalysts may be used singly or in combinations of two or more.

Liquid ammonia, aqueous ammonia, or a methanol solution of ammonia may be added to a reaction system for suppression of the generation of a secondary amine and a tertiary amine. In that case, the amount of ammonia added is, for example, 0.1 to 100 times, preferably 0.2 to 80 times, more preferably 0.3 to 60 times the mass of a compound represented by the general formula (6), although this is not limited thereto.

The reaction temperature of a hydrogen reduction reaction is, for example, 100 to 150° C., preferably 100 to 140° C., more preferably 100 to 130° C. As the reaction temperature increases, the decomposition reaction of a compound represented by the general formula (5) is accelerated. A temperature of 100° C. or lower causes the reaction to proceed slowly. The pressure of hydrogen is, for example, 3 to 50 kgf/cm$^2$, preferably 4 to 30 kgf/cm$^2$, more preferably 5 to 20 kgf/cm$^2$. The reaction is monitored by NMR, and the completion can be assumed when no change is observed in conversion ratio. After completion of the reaction, the used catalyst can be removed by filtration.

The following [Step 5] to [Step 8] are optional purifying steps. In the [Step 5], compounds (crude products) produced in the [Step 4] are reacted with a strong acid cation exchange resin, and then the strong acid cation exchange resin is washed with water or monohydric alcohol having 1 to 5 carbon atoms for separation of substances other than a compound represented by the general formula (1).

Specific examples of the strong acid cation exchange resin used in the [Step 5] include AMBERLITE series (IR120B, IR124B, 200CT, and 252) made by Organo Corporation, AMBERJET series (1020, 1024, 1060, and 1220) made by Organo Corporation, DIAION series (e.g. SK104, SK1B, SK110, SK112, PK208, PK212, PK216, PK218, PK220, PK228, UBK08, UBK10, UBK12, UBK510L, UBK530, and UBK550) by Mitsubishi Chemical Corporation, DOWEX series (50 W×2 50-100, 50 W×2 100-200, 50 W×4 100-200, 50 W×8 50-100, 50 W×8 100-200, 50 W×8 200-400, HCR-S, and HCR-W2(H)) made by Dow Chemical Co., although this is not limited thereto. The amount of the strong acid cation exchange resin used is, for example, 1 to 50 times, preferably 1 to 30 times, more preferably 1 to 20 times the mass of a compound represented by the general formula (1).

In the case of using a strong acid cation exchange resin, the strong acid ion exchange resin may be treated with an acid compound prior to use. Since commercially available strong acid cation exchange resins are often in an alkali metal sulfonate salt state, the pretreatment with an acid compound regenerates sulfo groups, so that the reaction efficiency can be improved. Examples of the acid compound for use include inorganic acids such as hydrochloric acid, sulfuric acid, nitric acid, phosphoric acid, and perchloric acid, although this is not limited thereto. The amount of the acid compound used is, for example, 1 to 15 times, preferably 1 to 10 times, more preferably 1 to 8 times the mass of the strong acid cation exchange resin. After treatment of the strong acid cation exchange resin with an acid compound, the acid compound is separated from the resin by water washing, and water is separated by a water-soluble organic solvent such as methanol and ethanol as needed.

Examples of the method for reacting the compounds (crude products) obtained in the [Step 4] with a strong acid cation exchange resin include: flowing the solution of the crude products in a column filled with the ion exchange resin to cause adsorption; and circulating the solution of the crude products between a cartridge filled with the resin and the reaction tank for the step 4; although this is not particularly limited.

The strong acid cation exchange resin with an adsorbed compound represented by the general formula (1) is then washed with water or a monohydric alcohol having 1 to 5 carbon atoms, so that compounds other than the target substance can be separated. Examples of the monohydric alcohol having 1 to 5 carbon atoms include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol. In performing washing, water or a monohydric alcohol may be used alone, or a mixture of water and one or more alcohols or a mixture of two or more alcohols may be used. In that case, the mixing ratio is not particularly limited. The amount of water or a monohydric alcohol having 1 to 5 carbon atoms or a mixture thereof used is, for example, 1 to 30 times, preferably 1 to 20 times, more preferably 1 to 10 times the mass of the strong acid cation exchange resin for use, although this is not particularly limited.

In the [Step 6], the strong acid cation exchange resin with an adsorbed compound represented by the general formula (1) is reacted with a basic compound in water or a monohydric alcohol having 1 to 5 carbon atoms, so that a compound represented by the general formula (1) is extracted in the monohydric alcohol. In performing the reaction, water or the monohydric alcohol may be used alone, or a mixture of water and one or more alcohols or a mixture of two or more alcohols may be used. In that case, the mixing ratio is not particularly limited. Examples of the method for reacting a strong acid cation exchange resin and a basic compound include: flowing the solution of the basic compound in a column filled with the ion exchange resin to cause reaction as in the [Step 5]; and circulating the solution of the basic compound between a cartridge filled with the ion exchange resin and the reaction tank for the [Step 4] and [Step 5]; although this is not particularly limited.

Specific examples of the monohydric alcohol for use in the [Step 6] include methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol. The amount of water or a monohydric alcohol used is, for example, 1 to 30 times, preferably 1 to 20 times, more preferably 1 to 10 times the mass of the strong acid cation exchange resin for use, although this is not particularly limited.

As the basic compound for use in the [Step 6], ammonia dissolved in water or an organic solvent (e.g. ammonia water and methanol solution of ammonia) may be suitably used, and primary, secondary and tertiary aliphatic amines, mixed amines, aromatic amines, and heterocyclic amines may be also used. Examples of the primary aliphatic amines include methylamine, ethylamine, n-propylamine, isopropylamine, n-butylamine, isobutylamine, sec-butylamine, tert-butylamine, and ethylene diamine; examples of the secondary aliphatic amines include dimethylamine, diethylamine, di-n- propylamine, diisopropylamine, di-n-butylamine, diisobutylamine, di-sec-butylamine; examples of the tertiary aliphatic amines include trimethylamine, triethylamine, tri-n-propylamine, triisopropylamine, tri-n-butylamine, tri-isobutylamine, and tri-sec-butylamine; examples of the mixed amines include dimethylethylamine, methylethylpropylamine, benzylamino, phenethylamine, benzyldimethylamine; specific examples of the aromatic amines and the heterocyclic amines include aniline derivatives (e.g. aniline, N-methylaniline, N-ethylaniline, N-propylaniline, N,N-dimethylaniline, 2-methylaniline, 3-methylaniline, 4-methylaniline, ethylaniline, propylaniline, trimethylaniline, 2-nitroaniline, 3-nitroaniline, 4-nitroaniline, 2,4-dinitroaniline, 2,6-dinitroaniline, 3,5-dinitroaniline, and N,N-dimethyltoluidine), diphenyl(p-tolyl)amine, methyldiphenylamine, triphenylamine, phenylenediamine, naphthylamine, diaminonaphthalene, and pyridine derivatives (e.g. pyridine, methylpyridine, ethylpyridine, propylpyridine, butylpyridine, 4-(1-butylpentyl)pyridine, dimethylpyridine, trimethylpyridine, triethylpyridine, phenylpyridine, 3-methyl-2-phenylpyridine, 4-tert-butylpyridine, diphenylpyridine, benzylpyridine, methoxypyridine, butoxypyridine, dimethoxypyridine, 4-pyrrolidinopyridine, 2-(1-ethylpropyl)pyridine, aminopyridine, and dimethylaminopyridine), although this is not limited thereto. Alternatively an alkali aqueous solution such as potassium hydroxide and sodium hydroxide may be used as a basic compound. The amount of the basic compound used is, for example, 0.1 to 100 times, preferably 0.1 to 10 times, more preferably 0.1 to 5 times the amount of the resin for use.

In the [Step 7], after concentration of the reaction liquid in the [Step 6], the solvent is substituted with a good solvent for a compound represented by the general formula (1) contained in the reaction liquid, such that the concentration of a compound represented by the general formula (1) is adjusted to be 10 to 50 mass %.

Examples of the good solvent for a compound represented by the general formula (1) for use in the [Step 7] include THF and the same good solvents as exemplified in the step 3, although this is not limited thereto. The good solvents may be used singly or in combinations of two or more. In that case, the mixing ratio is not particularly limited. After solvent substitution, the concentration is, for example, 10 to 50 mass %, preferably 15 to 45 mass %, more preferably 20 to 40 mass %.

In the [Step 8], the solution produced by concentration in the [Step 7] is dripped into a poor solvent for a compound represented by the general formula (1) to be crystallized. A compound represented by the general formula (1) is thereby produced.

The poor solvent for use in the [Step 8] has a low solubility for a compound represented by the general formula (1). Specific examples of the poor solvent include the same poor solvents as exemplified in the step 3, although this is not limited thereto. The amount of the poor solvent used is, for example, 5 to 100 times, preferably 5 to 50 times, more preferably 5 to 20 times the mass of the compound represented by the general formula (5), although this is not limited thereto. The poor solvents may be used singly or in combinations of two or more. The different solvents for mixing may the same different solvents as exemplified in the step 3, although this is not limited thereto. In the case of mixed use, the mixing ratio is not particularly limited.

In the [Step 8], after precipitation of solid by crystallization, the solid may be washed for purification as needed. Preferably the solvent for use in washing is the same poor solvent as described above, although this is not particularly limited, without particular limitation on the amount of the washing solvent used. The obtained solid is dried under reduced pressure, so that a compound represented by the general formula (1) can be extracted as solid.

In the operation after the [Step 6], a step of freeze drying is required when a compound represented by the general formula (1) is extracted as aqueous solution. Special facilities are required for freeze drying and a long time is required for complete removal of water, so that an industrial-scale production is difficult. In the present invention, however, the purification using an organic solvent allows for simplified facilities and processes.

EXAMPLES

The present invention is specifically illustrated with reference to the following Examples and Comparative Examples, though the present invention is not limited to the following Examples. In the notation of molecular weight in Examples, the weight average molecular weight (Mw) and the number average molecular weight (Mn) are values in terms of polyethylene glycol measured by GPC. Measurement by GPC was performed under the following conditions:

Column: TSK gel Super AWM-H, Super AW-3000
Developing solvent: DMF (0.01 mol/L lithium bromide solution)
Column oven temperature: 60° C.
Sample concentration: 0.20 wt. %
Sample injection volume: 25 µl
Flow rate: 0.3 ml/min

Synthesis Example 1

Synthesis of Polymerization Initiator (3A)

After placement of a stirring bar in a 500 mL two neck round-bottom flask, a rectification tube, a thermometer, a Liebig condenser, a fractionating column, two 50 mL round-bottom flasks, and one 300 mL two neck flask were connected, so that a distillation device was assembled. After the degree of vacuum in the device was held at 10 Pa or less, the internal part of the device was heated with an oil bath and a heat gun, so that the water content in the system was removed. Subsequently diethylene glycol monomethyl ether (Tokyo Chemical Industry Co., Ltd.) was injected into the 500 mL two neck round-bottom flask under nitrogen stream, and reduced-pressure distillation was performed. The measured water content ratio was 1 ppm or less after distillation.

After placement of a stirring bar in a 3 L two neck round-bottom flask, a rectification tube, a thermometer, a Dimroth condenser, a fractionating column, a 200 mL round-bottom flask, and a 2 L two neck flask were connected, so that a distillation device was assembled. After the degree of vacuum in the device was held at 10 Pa or less, the internal part of the device was heated with an oil bath and a heat gun, so that the water content in the system was removed. Subsequently dehydrated THF (Kanto Chemical Co., Ltd.), metal sodium pieces (Kanto Chemical Co., Ltd.), and benzophenone (Tokyo Chemical Industry Co., Ltd.) were injected into the 3 L two neck round-bottom flask under nitrogen stream, and refluxing was performed under normal pressure for 5 hours. After confirmation that the color in the 3 L two neck round-bottom flask changed into bluish purple, the distilled THF was taken out into the 2 L two neck flask. The measured water content ratio was 1 ppm or less after distillation.

In a glove box under a nitrogen atmosphere, 15.98 g of potassium hydride (in a mineral oil form, made by Kanto Chemical Co., Ltd.) was weighed and fed into a 500 mL four neck flask connected to a thermometer, a dripping funnel, and a Dimroth condenser under nitrogen stream. After the mineral oil in potassium hydride was washed with hexane, 127.65 g of distilled THF was added into the 500 mL four neck flask. Into the dripping funnel 18.73 g of distilled diethylene glycol monomethyl ether was injected to be dripped into the 500 mL four neck flask little by little. Maturation was performed for 2 hours, so that 148.62 g of THF solution of the polymerization initiator (3A) was produced. A reaction scheme is shown in the following.

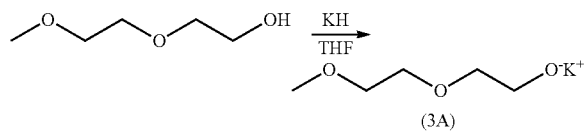

(3A)

Polymer Synthesis Example 1

Synthesis of Polymer (4A)

A stirring bar was placed in a 2 L four neck flask connected to a thermometer, a dripping funnel, and a Dimroth condenser. After the degree of vacuum in the device was held at 10 Pa or less, the internal part of the device was heated with an oil bath and a heat gun, so that the water content in the system was removed. Subsequently 3.60 g of the polymerization initiator (3A) and 420 g of distilled THF were added into the 2 L four neck flask under nitrogen stream.

Into the dripping funnel, 60 g of ethylene oxide and 120 g of distilled THF were injected, to be dripped into the 2 L four neck flask little by little. After confirming stabilization of the temperature in the 2 L four neck flask, the 2 L four neck flask was immersed in an oil bath held at a temperature of 45° C. for maturation for 8 hours. After completion of the reaction, the oil bath was detached and the reaction system was cooled to the room temperature. A reaction scheme is shown in the following.

A small amount of the obtained reaction system was sampled and quenched with acetic acid for measurement by GPC. The following results were obtained: Mw=8,500 and Mw/Mn=1.04.

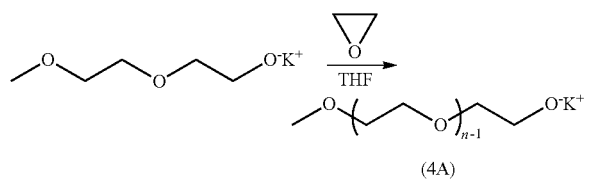

(4A)

Polymer Synthesis Example 2

Synthesis of Polymer (5A)

A stirring bar was placed in a 500 mL four neck flask connected to a thermometer, a Dimroth condenser, a fractionating column, and a 300 mL round-bottom flask. After the degree of vacuum in the device was held at 10 Pa or less, internal part of the device was heated with an oil bath and a heat gun, so that the water content in the system was removed. The THF solution of the polymer (4A) (10 g in terms of solid content) was fractionated with a syringe and fed into the 500 mL four neck flask under nitrogen stream. With the temperature in the 500 mL four neck flask being held at 40° C. or lower, the polymer solution was concentrated and adjusted to be a solid content concentration of 25 wt. %.

Under nitrogen stream, 1.0 g of acrylonitrile was fed in the 500 mL four neck flask, so that maturation was performed for 3 hours, with the temperature in the 500 mL four neck flask being kept at 40° C. After completion of the reaction, the oil bath was detached and the reaction system was cooled to room temperature. After addition of 0.2 g of acetic acid into the system for quenching, 10 g of an alkali adsorbent "KYOWADO 700" (Kyowa Chemical Industry Co., Ltd.) was added for performing a reaction for 3 hours. After filtration of the alkali adsorbent, the filtrate was transferred into a 300 mL round-bottom flask and concentrated to a solid content concentration of a polymer (5A) of 25 wt. % with a rotary evaporator.

In a 500 mL beaker with a stirring bar therein, 100 g of hexane and 50 g of ethyl acetate were mixed. After dripping of the concentrated liquid for 10 minutes with a dripping funnel, maturation was performed for 20 minutes. The obtained white powder was filtered and then returned to the original beaker, to be washed with a mixed solvent of 50 g of hexane and 25 g of ethyl acetate for 20 minutes. Then, the same washing operation was further performed once. A reaction scheme is shown in the following.

The obtained white powder was vacuum-dried to obtain 9.12 g of a polymer (5A). The following GPC measurement results were obtained: Mw=8,800 and Mw/Mn=1.05.

It is revealed that the present synthesis example has a substantially simplified process, compared with a common method including the successive steps of quenching the polymer (4A) with an acid, crystallizing and purifying the produced polyethylene glycol derivative, and reacting with acrylonitrile in the presence of a base.

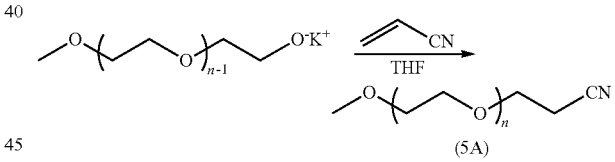

(5A)

Polymer Synthesis Example 3

Synthesis of Polymer (1A)

Into a 100 mL autoclave for hydrogen reduction, 5.0 g of a polymer (5A), 5.0 g of Raney cobalt catalyst R-400 (Nikko Rica Corporation), and 10.0 g of methanol were injected, and ammonia gas (pressure: 3 kg/cm$^2$) was enclosed at room temperature. Subsequently hydrogen gas (pressure: 10 kg/cm$^2$) was enclosed, and the inner temperature was raised to 120° C. for a direct reaction for 6 hours. After cooling to room temperature, the pressure was returned to atmospheric pressure. Subsequently nitrogen was blown in for removal of ammonia in the system. After removal of the Raney cobalt catalyst by filtration, the filtrate was transferred into a 100 mL round-bottom flask, and ammonia and methanol were distilled away with a rotary evaporator. Through vacuum concentration almost to dryness, the solid content concentration of the polymer (1A) was adjusted to 5 wt. %.

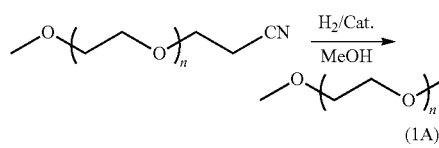

Polymer Synthesis Example 4

Purification of Polymer (1A)

The inside of a cartridge filled with 50 g of a cation exchange resin DIAION PK-208 (Mitsubishi Chemical Corporation) was washed with 300 g of 1N hydrochloric acid, and then washed 3 times with 300 g of ion-exchanged water, and subsequently once with 300 g of methanol. Into a 500 mL two neck flask, 5 wt. % polymer (1A) solution in methanol was injected, and transferred into the cartridge with a pump. The methanol solution discharged from the liquid outlet of the cartridge was added into the original 500 mL round-bottom flask. The operation was continuously performed for 2 hours, so that the polymer (1A) was adsorbed to the cation exchange resin. Subsequently the resin in the cartridge was washed with 300 g of methanol once, and then the polymer (1A) was eluted from the cation exchange resin with 50 g of 7N ammonia solution (methanol solution made by Kanto Chemical Co., Ltd.).

The eluent was transferred into a 500 mL round-bottom flask, and ammonia and methanol were distilled away with a rotary evaporator. Through vacuum concentration almost to dryness, the solvent was substituted with toluene such that the solid content concentration of the polymer (1A) was adjusted to 25 wt. %

In a 500 mL beaker with a stirring bar therein, 100 g of hexane and 50 g of ethyl acetate were mixed. After dripping of 25 wt. % produced polymer (1A) solution was dripped for 10 minutes with a dripping funnel, stirred for 20 minutes, and maturation was performed. The obtained white powder was filtered and then returned to the original beaker, to be washed with a mixed solvent of 50 g of hexane and 25 g of ethyl acetate for 20 minutes. And the same washing operation was further performed once.

The obtained white powder was vacuum-dried to obtain 8.51 g of a polymer (1A). The following GPC measurement results were obtained: Mw=8,500 and Mw/Mn=1.05.

Polymer Synthesis Example 5

Synthesis of Polymers (4B) to (4F)

Polymers (4B) to (4F) were synthesized by an approximately the same operations as in the [Polymer Synthesis Example 1], except that the amount of the polymerization initiator used was changed. The analysis results are shown in Table 1.

TABLE 1

|  | Amount of polymerization initiator (g) | Mw | Mw/Mn |
| --- | --- | --- | --- |
| Polymer (4A) | 3.60 | 8,500 | 1.04 |
| Polymer (4B) | 3.45 | 8,800 | 1.05 |
| Polymer (4C) | 3.30 | 9,200 | 1.06 |

TABLE 1-continued

|  | Amount of polymerization initiator (g) | Mw | Mw/Mn |
| --- | --- | --- | --- |
| Polymer (4D) | 3.00 | 9,900 | 1.07 |
| Polymer (4E) | 2.60 | 11,300 | 1.06 |
| Polymer (4F) | 2.20 | 13,400 | 1.05 |

Polymer Synthesis Example 6

Synthesis of Polymers (5B) to (5F)

Polymers (5B) to (5F) were synthesized by an approximately the same operations as in the [Polymer Synthesis Example 2], except that the polymer (4A) as starting material was changed to the polymers (4B) to (4F). The analysis results are shown in Table 2.

TABLE 2

|  | Mw | Mw/Mn | Starting polymer |
| --- | --- | --- | --- |
| Polymer (5A) | 8,800 | 1.05 | Polymer (4A) |
| Polymer (5B) | 9,000 | 1.05 | Polymer (4B) |
| Polymer (5C) | 9,300 | 1.06 | Polymer (4C) |
| Polymer (5D) | 9,900 | 1.07 | Polymer (4D) |
| Polymer (5E) | 11,500 | 1.06 | Polymer (4E) |
| Polymer (5F) | 13,800 | 1.05 | Polymer (4F) |

Polymer Synthesis Example 7

Synthesis of Polymers (1B) to (1F)

Polymers (1B) to (1F) were synthesized by an approximately the same operations as in the [Polymer Synthesis Example 3] and the [Polymer Synthesis Example 4], except that the polymer (5A) as starting material was changed. The analysis results are shown in Table 3.

TABLE 3

|  | Mw | Mw/Mn | Starting polymer |
| --- | --- | --- | --- |
| Polymer (1A) | 8,500 | 1.05 | Polymer (5A) |
| Polymer (1B) | 8,900 | 1.05 | Polymer (5B) |
| Polymer (1C) | 9,300 | 1.06 | Polymer (5C) |
| Polymer (1D) | 9,800 | 1.07 | Polymer (5D) |
| Polymer (1E) | 11,500 | 1.06 | Polymer (5E) |
| Polymer (1F) | 13,700 | 1.05 | Polymer (5F) |

Comparative Polymer Synthesis Example 1

A stirring bar and 0.07 g of potassium methoxide (Kanto Chemical Co., Ltd.) as a polymerization initiator was placed in a 500 mL four neck round-bottom flask connected to a thermometer, a dripping funnel, and a Dimroth condenser. After the degree of vacuum in the device was held at 10 Pa or less, the internal part of the device was heated with an oil bath and a heat gun, so that the water content in the system was removed.

Subsequently 40 μL of methanol (Tokyo Chemical Industry Co., Ltd.) and 140 g of distilled THF were injected in the four neck flask under nitrogen stream, and the mixture was agitated at room temperature until potassium methoxide was completely dissolved.

Into the dripping funnel, a mixed solution of 35 g of ethylene oxide and 60 g of distilled THF were injected, to be dripped into the four neck flask little by little, with the inner temperature being kept at 35° C. or lower. After dripping of the whole quantity, the mixture was agitated for 80 hours, with the inner temperature being kept at 50° C. or lower.

After confirming no change in conversion ratio of ethylene oxide, 0.06 g of acetic acid was added into the flask. After removal of ethylene oxide by nitrogen bubbling, the reaction liquid was transferred into a 500 mL round-bottom flask, and concentrated until solid is precipitated with a rotary evaporator. The crude product of polymer in an amount of 23 g was redissolved in 46 g of toluene, and transferred into a dripping funnel.

Into a 500 mL beaker with a stirring bar therein, 138 g of isopropyl alcohol was injected. After dripping of the polymer solution for 10 minutes with a dripping funnel, maturation was performed for 20 minutes. The obtained white powder was filtered and returned to the original beaker, to be washed with a mixed solvent of 69 g of isopropyl ether for 20 minutes. Then, the same washing operation was further performed twice.

The obtained white powder was vacuum-dried to obtain 18.54 g of a polymer (comparative polymer 1). The following GPC measurement results were obtained: Mw=7,200 and Mw/Mn=1.16.

It is shown that, in Polymer Synthesis Example 1 and Comparative Polymer Synthesis Example 1, while the latter required a long polymerization time of 80 hours, the former allowed the polymerization reaction to be completed within 8 hours by using the polymerization initiator soluble in THF. In other words, the method of the present invention achieves polymerization of ethylene oxide under mild conditions. In the Polymer Synthesis Example 2, the reaction liquid in the Polymer Synthesis Example 1 was directly used in the reaction, so that the process was substantially simplified. Furthermore, in the Polymer Synthesis Example 4, an organic solvent was used for purification of the resin with use of an ion-exchanged resin, so that purification of the polymer can be performed by a simple method without use of freeze-drying in the final process.

The method for producing an amino group-containing narrow molecular weight distribution polyethylene glycol derivative of the present invention provides a raw material of block copolymers for use in medical supplies and cosmetic products.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

What is claimed is:

1. A method for producing a narrow molecular weight distribution polyethylene glycol derivative having an amino group at an end represented by a general formula (1) comprising the steps of:

(1)

wherein n represents an integer of 1 to 450;

1) a step of reacting a compound represented by the general formula (2) with an alkali metal compound selected from M, M$^+$H$^-$, and RO$^-$M$^+$ (wherein M represents sodium (Na) or potassium (K), and R represents a monovalent alkyl group having 1 to 6 carbon atoms) to obtain a compound represented by a general formula (3):

(2)

wherein k represents an integer of 2 to 5;

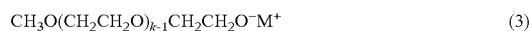

(3)

wherein k is the same as defined in the general formula (2); and

M is the same as defined for the alkali metal compound;

2) a step of dissolving a compound represented by the general formula (3) in tetrahydrofuran and then reacting with ethylene oxide to obtain a compound represented by the general formula (4):

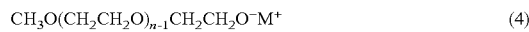

(4)

wherein n is the same as defined in the general formula (1);

3) a step of reacting the compound represented by the general formula (4) with acrylonitrile without further step of purifying the compound represented by the general formula (4) and then with an acid compound to obtain a compound represented by the general formula (5); and

(5)

4) a step of reducing a compound represented by the general formula (5) to obtain a compound represented by the general formula (1).

2. The method according to claim 1, wherein the step 2) is performed without using an alcohol co-solvent.

3. The method according to claim 1, wherein the step 2) is performed at a reaction temperature of 30 to 60° C.

4. The method according to claim 1, wherein the step 3) is performed at a reaction temperature of 20 to 60° C.

5. The method according to claim 1, wherein the compound represented by the general formula (2) has a k of 2 to 3, and the molar ratio between the compound represented by the general formula (2) and the compound represented by the general formula (3) is 0:100 to 20:80 after completion of the step 1).

6. The method according to claim 1, wherein the amount of acrylonitrile used in the step 3) is 1 to 50 equivalents relative to the number of moles of the compound represented by the general formula (4).

7. The method according to claim 1, wherein the acid compound in the step 3) is one or more selected from the group consisting of carboxylic acids, inorganic acids, sulfonic acids, and solid acids, and the amount of the acid compound used is 1 to 5 equivalents relative to the number of moles of the compound represented by the general formula (4).

8. The method according to claim 1, further comprising the step of separating an alkali metal salt produced by neutralization reaction with the acid compound in the step 3), with use of an alkali adsorbent.

9. The method according to claim 1, wherein the reduction in the step 4) is performed in a monohydric alcohol having 1 to 5 carbon atoms;

the monohydric alcohol having 1 to 5 carbon atoms is one or more selected from the group consisting of methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol; and the amount of the monohydric alcohol having 1 to 5 carbon atoms used is 0.2 to 50 times the mass of the compound represented by the general formula (5).

10. The method according to claim 1, wherein the reduction in the step 4) is performed with use of one or more hydrogenation catalysts selected from the group consisting of a Raney cobalt catalyst, a Raney nickel catalyst, and a gold-palladium supported catalyst; and the amount of the catalyst(s) is 0.1 to 5 times the mass of the compound represented by the general formula (5).

11. The method according to claim 1, further comprising the following steps after the step 4):
   5) a step of reacting a product in step 4) with a strong acid ion exchange resin and then washing the strong acid cation exchange resin to separate a substance other than the compound represented by the general formula (1);
   6) a step of reacting the ion exchange resin with a basic compound to separate the compound represented by the general formula (1);
   7) a step of concentrating a reaction liquid obtained in the step 6); and
   8) a step of dripping a concentrated liquid obtained in the step 7) into a poor solvent for the compound represented by the general formula (1) to be crystallized, thereby producing the compound represented by the general formula (1).

12. The method according to claim 11, wherein the amount of the strong acid ion exchange resin used in the step 5) is 1 to 50 times the mass of the compound represented by the general formula (1).

13. The method according to claim 11, wherein the strong acid cation exchange resin is washed with water or a monohydric alcohol having 1 to 5 carbon atoms in the step 5);
   the monohydric alcohol having 1 to 5 carbon atoms is one or more selected from the group consisting of methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol; and
   the amount of the monohydric alcohol having 1 to 5 carbon atoms used is 1 to 30 times the mass of the ion exchange resin.

14. The method according to claim 11, wherein the reaction with the basic compound in the step 6) is performed with use of water or a monohydric alcohol having 1 to 5 carbon atoms;
   the monohydric alcohol having 1 to 5 carbon atoms is one or more selected from the group consisting of methanol, ethanol, n-propyl alcohol, isopropyl alcohol, n-butyl alcohol, sec-butyl alcohol, tert-butyl alcohol, n-pentyl alcohol, isopentyl alcohol, and neopentyl alcohol; and
   the amount of the monohydric alcohol having 1 to 5 carbon atoms used is 1 to 30 times the mass of the ion exchange resin.

15. The method according to claim 11, wherein the basic compound in the step 6) is one or more selected from the group consisting of ammonia, primary, secondary, and tertiary aliphatic amines, mixed amines, aromatic amines, heterocyclic amines; and
   the amount of the basic compound used is 0.1 to 100 times the mass of the ion exchange resin.

16. The method according to claim 11, further comprising a solvent substitution step of substituting the concentrated reaction liquid in the step 7) with a good solvent for the compound represented by the general formula (1), wherein
   the good solvent is one or more selected from the group consisting of THF, 1,4-dioxane, benzene, toluene, xylene, ethyl acetate, n-butyl acetate, γ-butyrolactone, acetone, methyl ethyl ketone, methyl isobutyl ketone, dimethyl sulfoxide (DMSO), N,N-dimethylformamide (DMF), and acetonitrile; and
   the concentration of the compound represented by the general formula (1) after solvent substitution is 10 to 50 mass %.

17. The method according to claim 11, wherein the poor solvent for the compound represented by the general formula (1) in the step 8) is one or more selected from the group consisting of n-hexane, heptane, octane, nonane, decane, cyclopentane, cyclohexane, cycloheptane, cyclooctane, diethyl ether, diisopropyl ether, and di-n-butyl ether; and
   the amount of the poor solvent used is 5 to 100 times the mass of the compound represented by the general formula (1).

* * * * *